(12) United States Patent
Butani et al.

(10) Patent No.: US 10,598,610 B1
(45) Date of Patent: Mar. 24, 2020

(54) METHODS AND SYSTEMS FOR IMAGING AND ANALYZING WOOD BLANKS AND BILLETS

(71) Applicant: Kub Technologies, Inc., Stratford, CT (US)

(72) Inventors: Vikram Butani, Stratford, CT (US); Yan Chen, Stratford, CT (US); Chester Lowe, Stratford, CT (US); Vignesh Mandalapa-Bhoopathy, Stratford, CT (US); Edwin Maria-Selvaraj, Stratford, CT (US); Roberto Velasco, Stratford, CT (US); Peter Yasutake, Stratford, CT (US)

(73) Assignee: KUB Technologies, Inc, Stratford, CT (US)

( * ) Notice: Subject to any disclaimer, the term of this patent is extended or adjusted under 35 U.S.C. 154(b) by 0 days.

(21) Appl. No.: 16/523,221

(22) Filed: Jul. 26, 2019

Related U.S. Application Data

(60) Provisional application No. 62/841,065, filed on Apr. 30, 2019.

(51) Int. Cl.
*G01N 23/04* (2018.01)
*G01N 23/18* (2018.01)

(52) U.S. Cl.
CPC ............. *G01N 23/04* (2013.01); *G01N 23/18* (2013.01); *G01N 2223/1016* (2013.01); *G01N 2223/405* (2013.01); *G01N 2223/408* (2013.01); *G01N 2223/601* (2013.01); *G01N 2223/619* (2013.01)

(58) Field of Classification Search
None
See application file for complete search history.

(56) References Cited

U.S. PATENT DOCUMENTS

| | | | | |
|---|---|---|---|---|
| 6,757,354 | B2* | 6/2004 | Skatter | G01B 15/04 378/10 |
| 7,149,633 | B2* | 12/2006 | Woods | G01N 23/18 702/40 |
| 7,769,131 | B2* | 8/2010 | Wallace | G01M 5/0025 378/54 |
| 8,073,106 | B2* | 12/2011 | Wallace | G01M 5/0025 378/89 |
| 9,524,546 | B2* | 12/2016 | Nagashima | G01N 23/04 |
| 9,805,461 | B2* | 10/2017 | Nagashima | G01N 23/04 |

(Continued)

*Primary Examiner* — Thomas R Artman
(74) *Attorney, Agent, or Firm* — Ziegler IP Law Group, LLC

(57) ABSTRACT

An X-ray system for analyzing materials includes an X-ray source, an X-ray detector and a sample platform, and a controller configured to generate a radiograph of material on the sample platform by selectively energizing the X-ray source to emit X-rays through the material to the X-ray detector along a scanned length of the material, calculate a plurality of measured density values along the scanned length of the material, calculate a plurality of model density values of the material from one or more of settings of the X-ray system, characteristics of the material along the scanned length of the material, and a longitudinal density variation for a particular application, compute a difference between the measured density values and the model density values and determine if the longitudinal density variation has been exceeded, and provide an alert as to whether the longitudinal density variation has been exceeded.

20 Claims, 9 Drawing Sheets

(56) References Cited

U.S. PATENT DOCUMENTS

| | | | |
|---|---|---|---|
| 2004/0057551 A1* | 3/2004 | Skatter | G01B 15/04 378/54 |
| 2005/0190958 A1* | 9/2005 | Woods | G01N 23/18 382/141 |
| 2008/0226027 A1* | 9/2008 | Wallace | G01M 5/0025 378/54 |
| 2010/0158190 A9* | 6/2010 | Wallace | G01M 5/0025 378/54 |
| 2010/0316191 A1* | 12/2010 | Wallace | G01M 5/0025 378/89 |
| 2017/0061598 A1* | 3/2017 | Nagashima | G01N 23/04 |

\* cited by examiner

METHODS AND SYSTEMS FOR IMAGING AND ANALYZING WOOD BLANKS AND BILLETS

CROSS-REFERENCE TO RELATED APPLICATIONS

This application claims priority to and the benefit of U.S. Provisional Patent Application Ser. No. 62/841,065 filed Apr. 30, 2019, the disclosure of which is incorporated herein by reference in its entirety.

FIELD

The disclosed embodiments relate to the field of utilizing an X-ray system to analyze material densitometry, in particular for analyzing wood blanks and billets utilized in the production of baseball bats.

BACKGROUND

The crack of a baseball against a wooden bat is a wonderful sound seldom heard today. Too often it's been replaced by the metallic "clink" of an aluminum bat. Baseball has its roots in balls, gloves and shoes made from animal hides, and bats made from trees. It seems an odd place for high tech equipment to intrude. Making a wooden bat returns you and your kids to the sound and feel of real, old-time baseball.

Almost every common wood has been used for bats at one time or another. However, a few species dominate the history of the sport. Traditionally northern ash has been the wood of choice, but currently—at least in professional baseball, —hard maple is equally desirable. Other materials may include bamboo, beech, birch, and hickory wood.

Bat blanks are graded not only for superior performance, but also for safety. A bat made from a graded bat blank is less likely to break in use. Bat blanks are graded differently from regular furniture grade lumber. First, only straight-grained wood from slow-growing trees of moderate size make the grade. The blank should have tight, evenly spaced growth rings and be free of flaws like knots. The best blanks are often split from the log rather than sawn in order to follow the grain perfectly. Extra care is taken in the drying of bat blanks to create an even distribution of moisture throughout the entire thickness.

While wood knots carry visual appeal, they adversely affect wood strength. Wood strength in knots can be assessed in two ways: tensile strength and compressive strength. These measurements provide a prediction as to how much load (weight) wood can safely bear before collapsing. Tensile stress attempts to elongate or expand an object, while compressive stress attempts to shorten or compress an object.

Since knots are defects which weaken lumber, this weakening effect is more serious when the lumber is subjected to forces perpendicular to the grain and/or tension than when under load along the grain and/or compression. Please note that the extent to which wood knots affect the strength of wood depends on their position, size, number, and condition.

As mentioned above, the most common wood for bats is White Ash (*Fraxinus americana*), a strong wood that has good resistance to impact strength, and is the correct density to make desirable weight baseball bats. The properties have contributed to making White Ash the most popular baseball bat wood for the past 100 years. It is well known that players are supposed to hit "LOGO UP" with an ash bat, so that ball contact is made on the edge-grain in order to prevent "flaking". Flaking occurs when repeated contact on the flat-grain results in the annual rings separating. Ash is susceptible to flaking because it is a ring porous species, where in a growth ring, pores formed early in the growing season are much larger than those formed later in the growing season.

According to conventional wisdom, ash bats that have approximately 8 to 10 rings per inch are most desirable and are stronger than other bats. FIG. 1 shows data from the Forest Products Laboratory of the United States Department of Agriculture Forest Service in the form of a graph with rings per inch on the x-axis versus modulus of elasticity on the y-axis for green White Ash wood blanks that were tested prior to the 1930's. Note that as the rings per inch increase, the modulus of elasticity of the tested wood drops. The solid vertical lines show a range of approx. 8 to 12 rings per inch, and the large dot is centered at 25 rings per inch. There is about a 20% drop between the data within the solid lines, and the large dot at 25 rings per inch.

FIG. 1 confirms the conventional wisdom that an ash bat with approx. 8 to 10 rings per inch has desirable modulus of elasticity properties and raises the possibility that the range could be expanded out to perhaps 8 to 12 rings per inch.

While ring-porous ash bats need to be hit on the edge grain because the annual rings will "flake" if hit repeatedly on the flat-grain, bats made of maple do not need to be hit on the edge grain, mainly because maple which is a diffuse porous species, which has pores that are essentially uniform within a ring.

In the 1960s, several species of wood were tested by the Forest Products Laboratory of the United States Department of Agriculture Forest Service for toughness (which is similar to impact bending—like a "karate chop" test). This was just a basic research report, but it was perfectly tailored for wood baseball bats and the results were convincing that wood is stronger when contact is made on the flat grain, even ash. The ash handle of a baseball bat is stronger when impact is made on the flat-grain of the barrel, but edge-grain contact is still advocated for ash bats because the annual rings in the barrel will fatigue and separate after repeated hits. The data in FIG. 1 also shows that rupture on the bark side of the wood is stronger than on the opposite face.

Radiography is considered the most cost-effective screening method for the detection of anomalies or weaknesses in wood blanks or billets. However, the resultant radiograph is subject to interpretation by the observer/operator. There are currently operators utilizing radiography to scan blanks or billets but it is observed that there is no system or method that utilizes computer aided detection to display and correlate observations.

SUMMARY

It would be advantageous in be able to scan the wood blanks or billets prior to turning by utilizing radiography to examine for internal anomalies or weaknesses and after capturing the radiograph, scanning the blank/billet X-ray scan utilizing a densitometry meter or histogram to verify integrity and homogeneity.

Currently it is believed that there is not a system or method incorporating an X-ray system to scan the wood blanks prior to turning and utilizing the analysis of densitometry and/or histogram.

In general, this disclosure may enable a device (X-ray system) utilizing a controller to capture a radiographic image of the sample being X-rayed and without intervention of the operator perform a quality control to verify integrity of the sample The advent of full-field digital detectors offers opportunities to develop advanced techniques for improved imaging of samples.

A device capturing both an X-ray image and performing a density analysis or histogram facilitates confirmation and orientation for the operator to verify internal as well as external integrity.

A histogram is a representation of the distribution of numerical data. Densitometry is the quantitative measurement of optical density in light-sensitive materials. Since density is usually measured by the decrease in the amount of light which shines through a material, utilizing the above densitometry and creating a histogram can be used to visualize opaque or non-opaque areas denoting weaknesses in the structure.

The disclosed embodiments may incorporate an X-ray system, (tube and detector) and a controller where the controller captures and analyzes the radiograph captured by the X-ray system.

The embodiments described above relate to baseball bat radiography but it should be understood that the disclosed embodiments are not isolated to baseball radiography but may be utilized for non-destructive testing, as well as any radiographic analysis, organic and non-organic, requiring an X-ray system, and is not limited to any sample fitting into or onto the confines of the X-ray system.

The disclosed embodiments relate to the field of an X-ray system incorporating an X-ray tube, an X-ray detector, and a controller for the production of organic and non-organic images. The controller receives X-ray data from the X-ray detector and determines, based on the X-ray data, the integrity of the wood blank or billet prior to the production of the resultant baseball bat. In particular, the disclosed embodiments relate to a system and method with corresponding apparatus for capturing an X-ray Image of a wood blank to verify integrity via both the radiograph and a densitometry scan/histogram.

According to at least one aspect of the disclosed embodiments, an X-ray system for analyzing materials includes an X-ray source, an X-ray detector and a sample platform, and a controller configured to: generate a radiograph of material on the sample platform by selectively energizing the X-ray source to emit X-rays through the material to the X-ray detector along a scanned length of the material; calculate a plurality of measured density values along the scanned length of the material; calculate a plurality of model density values of the material from one or more of settings of the X-ray system, characteristics of the material along the scanned length of the material, and a longitudinal density variation for a particular application; compute a difference between the measured density values and the model density values and determine if the longitudinal density variation has been exceeded; and provide an alert as to whether the longitudinal density variation has been exceeded.

The X-ray source may be a minimum 50 kVp and 1000 μa X-ray source.

The X-ray detector may include a rectangular array of approximately 4318×4320 pixels with a pixel size of 100 micrometers.

The controller may be configured to calculate the plurality of measured density values by averaging Gray values of detector pixels perpendicular to the scanned length of the material.

The material may include an organic or inorganic material.

The material may include one or more of wood, wood blanks, and wood billets.

The material may include one or more of baseball bats, softball bats, cricket bats, and table tennis bats.

The alert may include a message on a display of the controller.

The controller may be configured to concurrently display the radiograph and the plurality of measured density values.

The controller may be configured to display the plurality of measured density values overlaid on the radiograph.

According to one or more aspects of the disclosed embodiments, a method of using an X-ray system for analyzing materials, the X-ray system having an X-ray source, an X-ray detector and a sample platform, and a controller, the method including: generating a radiograph of material on the sample platform by selectively energizing the X-ray source to emit X-rays through the material to the X-ray detector along a scanned length of the material; calculating a plurality of measured density values along the scanned length of the material; calculating a plurality of model density values of the material from one or more of settings of the X-ray system, characteristics of the material along the scanned length of the material, and a longitudinal density variation for a particular application; computing a difference between the measured density values and the model density values and determine if the longitudinal density variation has been exceeded; and providing an alert as to whether the longitudinal density variation has been exceeded.

In the method, the X-ray source may be a minimum 50 kVp and 1000 μa X-ray source.

In the method, the X-ray detector may include a rectangular array of approximately 4318×4320 pixels with a pixel size of 100 micrometers.

The method may further include calculating the plurality of measured density values by averaging Gray values of detector pixels perpendicular to the scanned length of the material.

In the method, the material may include an organic or inorganic material.

In the method, the material may include one or more of wood, wood blanks, and wood billets.

In the method, the material may include one or more of baseball bats, softball bats, cricket bats, and table tennis bats.

In the method, the material may include providing an alert as a message on a display of the controller.

In the method, the material may include concurrently displaying the radiograph and the plurality of measured density values.

In the method, the material may include displaying the plurality of measured density values overlaid on the radiograph.

BRIEF DESCRIPTION OF THE DRAWINGS

To further clarify the above and other advantages and features of the disclosed embodiments, a more particular description of the disclosed embodiments will be rendered by reference to specific embodiments thereof that are illustrated in the appended drawings. It is appreciated that these drawings depict only typical embodiments and are therefore not to be considered limiting of its scope. The disclosed embodiments will be described and explained with additional specificity and detail through the use of the accompanying drawings in which.

DETAILED DESCRIPTION

Reference will now be made to the Figures wherein like structures will be provided with like reference designations. It is understood that the drawings are diagrammatic and schematic representations of exemplary embodiments and are not limiting of the disclosed embodiments nor are they necessarily drawn to scale. The Figures depict various features of the disclosed embodiments which are generally directed to a system that can utilize an X-ray system to capture an X-ray image of a sample and concurrently with the acquisition of the X-ray image verify integrity of the sample utilizing density analysis or a histogram.

As used herein, the term "controller," "controller system," or "processor" refers to any suitable device operable to accept input, process the input according to predefined rules, and produce output, including, for example, a server, workstation, personal controller, network controller, wireless telephone, personal digital assistant, one or more microprocessors within these or other devices, or any other suitable processing device with accessible memory. The controller may include input and output devices for receiving input from a user or a device and for providing alerts or notifications to a user or a device.

The term "controller program" or "software" refers to any non-transitory machine-readable instructions, program or library of routines capable of executing on a controller or controller system including controller readable program code.

Reference will now be made to the Figures wherein like structures will be provided with like reference designations. It is understood that the drawings are diagrammatic and schematic representations of exemplary embodiments of the disclosure, and are not limiting of the present disclosure nor are they necessarily drawn to scale.

Figure 2:
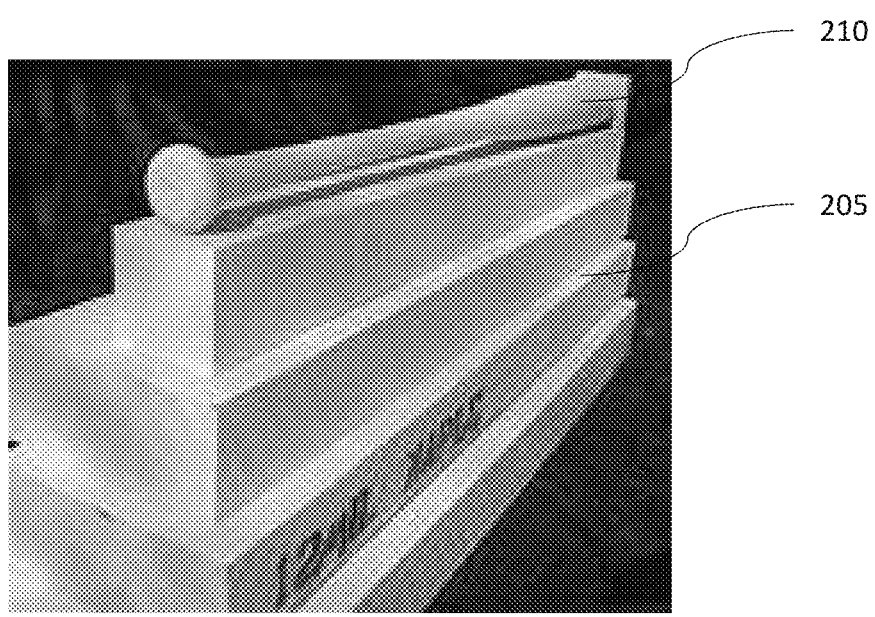
FIG. 2 illustrates examples of wood blanks and a finished baseball bat.
Figure 3:
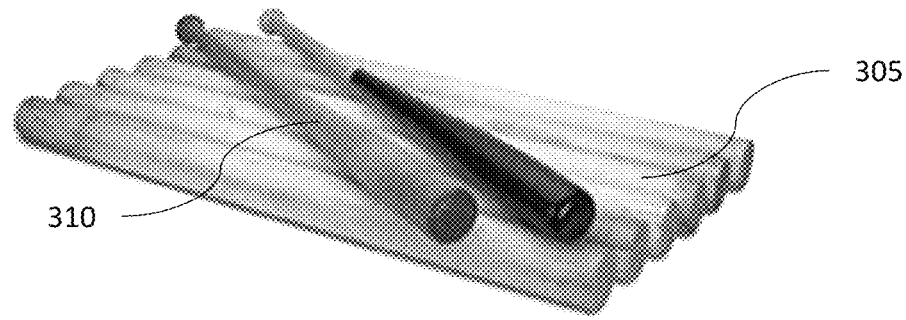
FIG. 3 illustrates examples of wood billets and a finished baseball bat.

The disclosed embodiments include a system and method for analyzing material at different stages of production or finishing, for example in the form of blanks which may be roughly cut or formed, or in the form of billets, which may be semi-finished or further finished blanks, or in the form of semi-finished pieces or finished pieces having a final shape. Using a baseball bat as an example, logs may be harvested and may typically be cut into 40 inch blanks, also referred to as splits. FIG. 2 shows examples of wood blanks 205 utilized for the production of baseball bats and an exemplary finished baseball bat 210. The splits may then be turned to produce rounded billets and then dried or seasoned. FIG. 3 shows examples of wood billets 305 utilized for the production of baseball bats and an exemplary finished baseball bat 310. In this example, the final object, or finished piece may be a baseball, softball, cricket, table tennis, or any other type of bat. The material may be inspected at any processing stage, for example, at the blank, billet, and finished bat stage, using the structures and techniques of the disclosed embodiments.

While the disclosed embodiments are discusses in terms of analyzing different components made of wood, it should be understood that the disclosed embodiments may be applicable for analyzing any material that has a density measurable using X-ray techniques. In some embodiments, the material may include any organic or inorganic material that fits within confines of the X-ray system.

Figure 4:
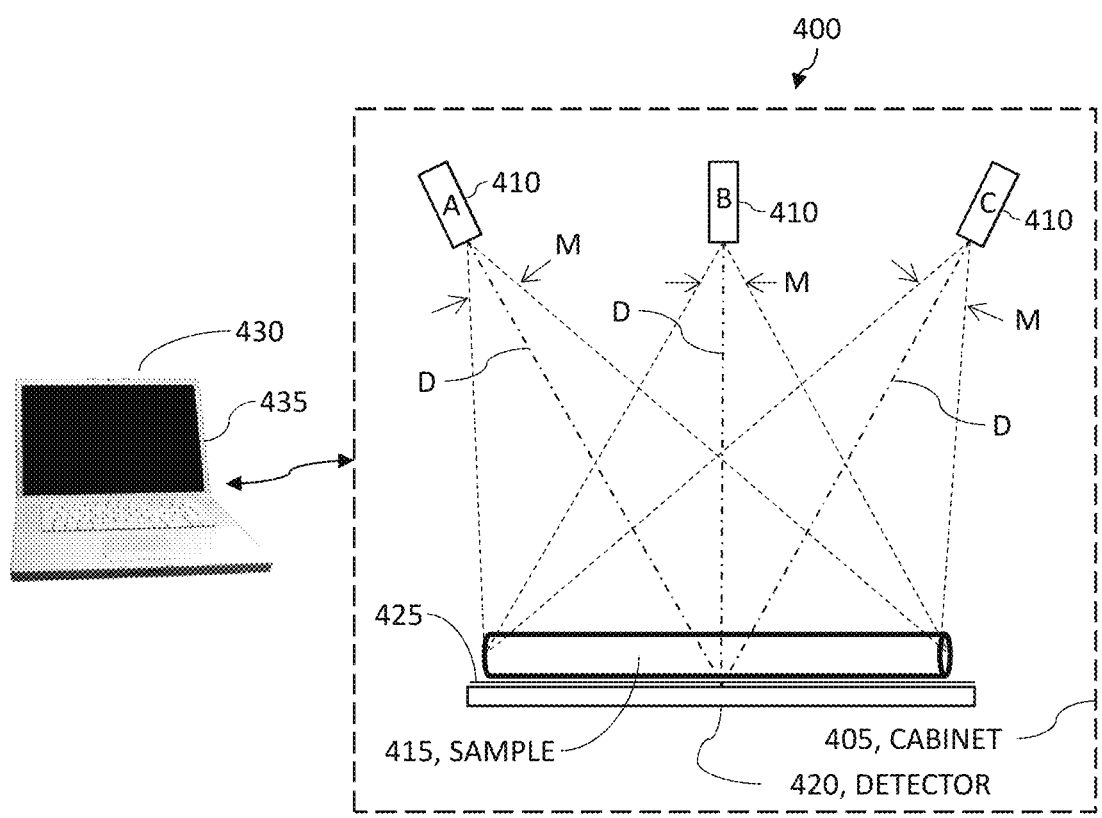
FIG. 4 shows a schematic diagram of an exemplary X-ray system for imaging a sample at different angles, according to the disclosed embodiments.

One embodiment of an X-ray system 400 incorporating aspects of the present disclosure is illustrated in FIG. 4. The X-ray system 400 may be three-dimensional specimen imaging system, capable of acquiring image data of a sample at multiple viewpoints, typically over an arc or linear path. A three-dimensional image may be derived by the reconstruction of the multiple image data.

In some embodiments the system 400 may be enclosed or housed in a cabinet 405, while in other embodiments, the system 400 may be free standing. Embodiments having a cabinet may include a moveable cabinet surrounding an interior chamber in which the X-ray system is enclosed and a door configured to provide access to the interior chamber.

Figure 1:
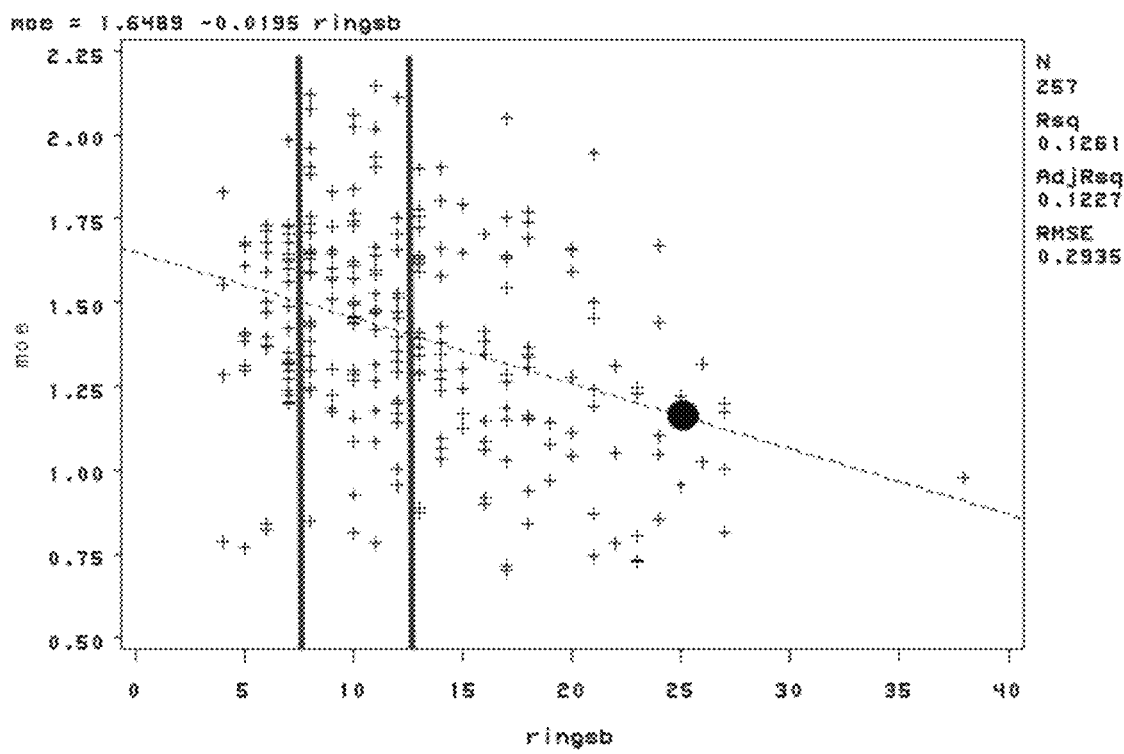
FIG. 1 shows data confirming that an ash bat with approx. 8 to 10 rings per inch has desirable modulus of elasticity properties.

In accordance with the aspects of the disclosed embodiments, an X-ray source 410 generates an X-ray beam and may include a swing arm, articulating arm or other movement mechanism for moving around a stationary sample 415, typically, but not necessarily, in an arc. References A, B, and C of FIG. 1 illustrate exemplary positions of the X-ray source 410 within the X-ray cabinet 405. The reference "D" at each of the positions A, B, C of the X-ray source 410 in FIG. 4 refers to a path of a point source of the X-ray beam. The reference "M" refers to the spread or fan of the X-ray beam.

The X-ray beam generally passes through the sample 415 and impinges on a detector 420. The detector 420 may include an array of pixels, the signals from which may be read to form images. The detector 420 may generate respective digital values for the pixels in a two-dimensional array. The size of the detector 420 may range, for example, from about 5 centimeters by 5 centimeters to about 47 centimeters by 47 centimeters. In one example, detector 420 may have a rectangular array of approximately 4318×4320 pixels with a pixel size of 100 micrometers.

The X-ray image data taken at from the detector 420 each of the number of exemplary positions A, B, C of the X-ray source 410 relative to the sample 415 may be processed to form images, where two or more of the differing image positions may be utilized to form a digital tomosynthesis image.

In one embodiment, the aspects of the present disclosure may limit the arc or linear travel of the X-ray source 410 over about a 20° to about a 50° arc. In some embodiments, the arc or linear travel may be limited to about 30°, and in further embodiments, the arc or linear travel may be limited to about 20°. The movement may be clockwise or counter clockwise along a path, which includes for example, one or more, or a combination thereof, of the following exemplary ranges: between approximately 350° (reference position A) to 0° (reference position B) to 10° (reference position C), or between approximately 340° (reference position A) to 0° (reference position B) to 20° (reference position C) and or between approximately 335° (reference position A) to 0° (reference position B) to 25° (reference position C). The ranges recited herein are intended to be approximate and inclusive of start and endpoints. In the example of FIG. 4, the X-ray source 410 may move such that the X-ray source 410, the detector 420, and the sample 415 may remain a fixed distance from each other. In some embodiments, the detector 420 may move or rotate, but the detector 420 may be maintained at a fixed distance relative to the sample 415 and X-ray source 410. In still other embodiments, the X-ray source 410 and the detector may both move while the X-ray source 410, the detector 420, and the sample 415 may remain a fixed distance from each other. The sample 415 may be disposed on or rest on a sample platform 425 which may be a protective cover or other surface of the detector 420.

In operation, the X-ray source 410 may be energized to emit an X-ray beam, generally throughout its travel along one or more of the paths or positions described above. The X-ray source 410 may operate in a range from about 0 kVp to about 90 kVp, and may be a 50 kVp 1000 µa X-ray source. The X-ray beam may travel through the sample 415 to the detector 420 and the multiple images collected at varying angles may be stored and then utilized for constructing a tomosynthesis image. In some embodiments, the multiple images collected at varying angles may be stored and then utilized for constructing a 2 dimensional radiograph image.

Movement of the X-ray source 410 and the detector 420, as well as energizing the X-ray source 410, reading data from the detector pixels, and processing the data to form images may be controlled by a controller 430 having a combination of one or more of software and hardware, such as non-transitory machine-readable instructions stored in a memory that are executable by one or more processors. In one embodiment, non-transitory machine readable instructions being executed by one or more processors of the controller 430 may be utilized to compile image data received from the detector 420 and present resulting images to a suitable display or monitor 435 at each imaging position, such as positions A, B, C. While the controller 430 is shown as freestanding near the system 400, it should be understood that the controller may be mounted to the optional cabinet 405, may be incorporated within the cabinet 405, or may be located remotely and may communicate using a network connection.

The image data attained at each respective position may be processed either at the full spatial resolution of detector 420 or at a lower spatial resolution by overlapping or binning a specified number of pixels in a single combined pixel value. For example, where the detector 420 may have a rectangular array of approximately 4318×4320 pixels with a pixel size of 100 micrometers, binning at a 2×2 ratio would result in an effective spatial resolution of approximately 200 micrometers. The binning may be achieved by one or more of the operation of the detector 420, or the controller 430.

Different embodiments of the present disclosure can utilize different ranges of motion of one or more of the X-ray source 410 and detector 420 as well as changing the angularity of one or both. The inventive aspects of the present disclosure differ from the prior art in that in prior art systems, either the detector and X-ray source 410 and/or the isocenter is above the sample and not at the detector surface. In accordance with the aspects of the present disclosure, in one embodiment, the X-ray source 410 may be configured to move, as described herein, while the detector 420 may be configured to remain stationary or in a fixed position.

The detector 420 and associated electronics may generate image data in digital form from each detector pixel at each of the angular positions, A, B, C of X-ray source 410 and translations positions of the detector 420 relative to the sample 415. While only three positions A, B, C are illustrated in FIG. 4, in practice more images may be taken at differing angles. For example, in one embodiment, images can be taken at approximately every 1° of rotation or motion of X-ray source 410.

Figure 5:
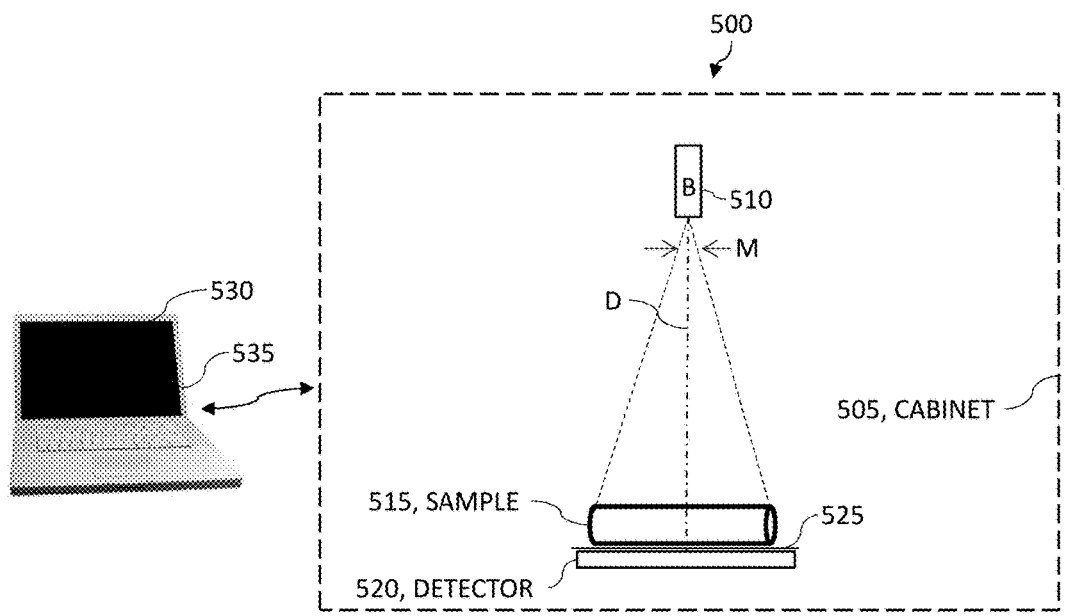
FIG. 5 shows a schematic diagram of an exemplary X-ray system for imaging a sample at a fixed angle, according to the disclosed embodiments.

FIG. 5 schematically illustrates another embodiment of an X-ray system 500 incorporating aspects of the present disclosure, where the X-ray source 510 may be located at approximately 0°, shown at reference point B in this example with the detector 520 oriented, or otherwise disposed, vertically below the X-ray source 510. In this embodiment, the X-ray source 510 and the detector 520 may generally scan in one direction, the X-ray source 510 or the detector 520 individually may generally scan in one direction while the other remains stationary, or both may remain stationary. The X-ray spread M in this example can be from about 0 kVp to about 50 kVp with the system preferably utilizing an automatic exposure control to ascertain the optimal setting to image the sample 515. In operation, X-ray source 510 may be energized to emit an X-ray beam at position B, or throughout a travel path if the X-ray source 510 is not stationary. The X-ray beam may travel through the sample 515 to the detector 520 and a 2-D image may be produced and stored by the controller 530. Similar to the embodiment shown in FIG. 4, the system 500 may be enclosed or housed in a cabinet 505, or in other embodiments may be free standing.

Figure 6:
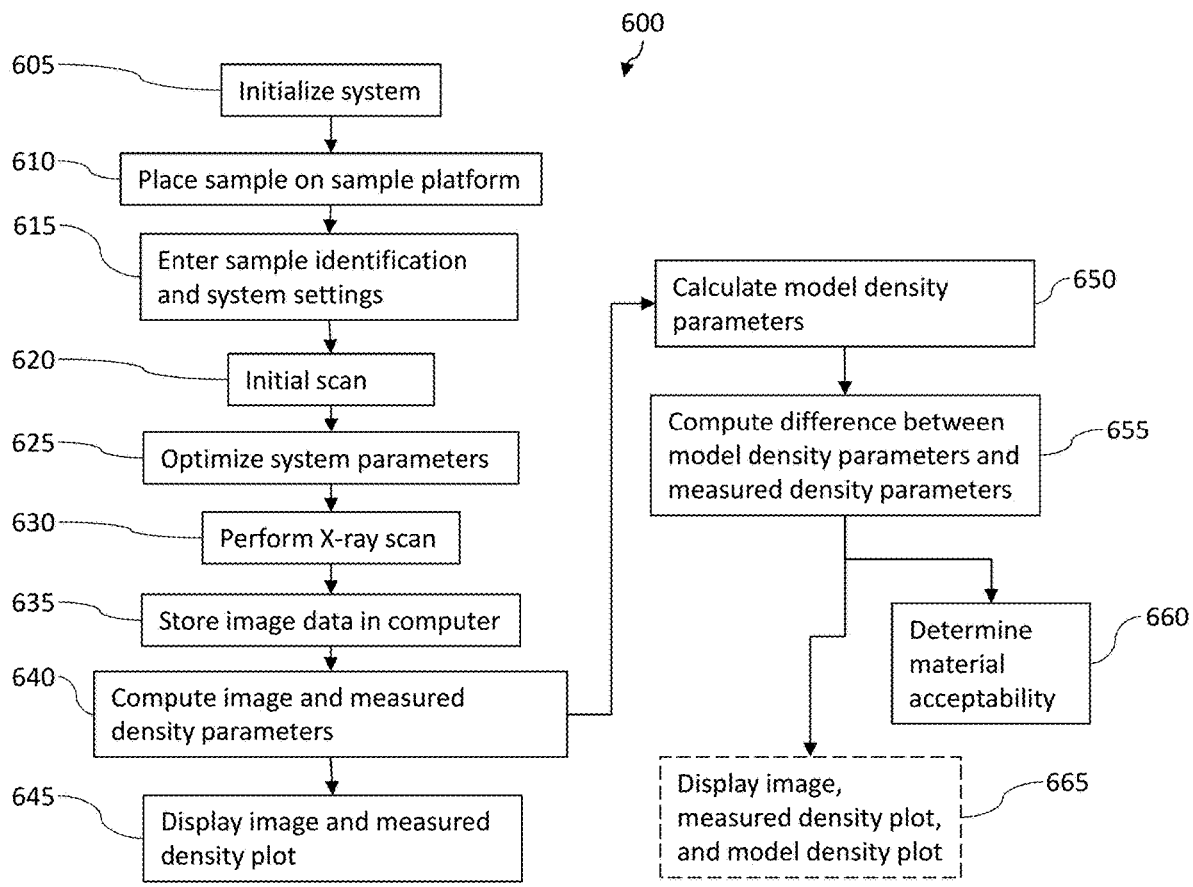
FIG. 6 illustrates an embodiment of an exemplary workflow for analyzing an exemplary sample according to the disclosed embodiments.

FIG. 6 illustrates an embodiment of an exemplary workflow 600 for analyzing an exemplary sample according to the disclosed embodiments. While shown and disclosed as applied to a finished bat, it should be understood that the exemplary workflow 600 may be utilized with any suitable material at any stage of production or finishing, for example in the form of blanks which may be roughly cut or formed, or in the form of billets, which may be semi-finished or further finished blanks, or in the form of finished pieces having a final shape. In some embodiments, the controller 430, 530 may be configured to perform the operations of the exemplary workflow 600 by controlling the operations of the X-ray source 410, 510, the X-ray detector 420, 520 and the sample platform 425, 525.

As shown in block 605, the X-ray system 400, 500 may be initialized, and the sample 415, 515 may be positioned on the sample platform 425, 525 as shown in block 610. Data and information regarding the sample 415, 515 including information about the sample material, X-ray system settings, and settings relevant to the imaging process and procedure may be entered into the controller 430, 530 as shown in block 615. As shown in block 620, an initial scan of the sample may be performed, and as shown in block 625, data from the initial scan may be used to optimize X-ray scanning parameters, such as the energy of the X-ray source 410, 510, movement of the X-ray source 410, 510, detector energizing and scanning parameters, movement of the detector 420, 520, if applicable, and any other suitable parameters of the X-ray system. As shown in block 630, the X-ray scan may be performed using the optimized parameters, and image data from the detector 420, 520 may be stored in the controller 430, 530 as shown in block 635. As shown in block 640, a radiograph image and measured density parameters or values of the material may be generated.

Figure 7:
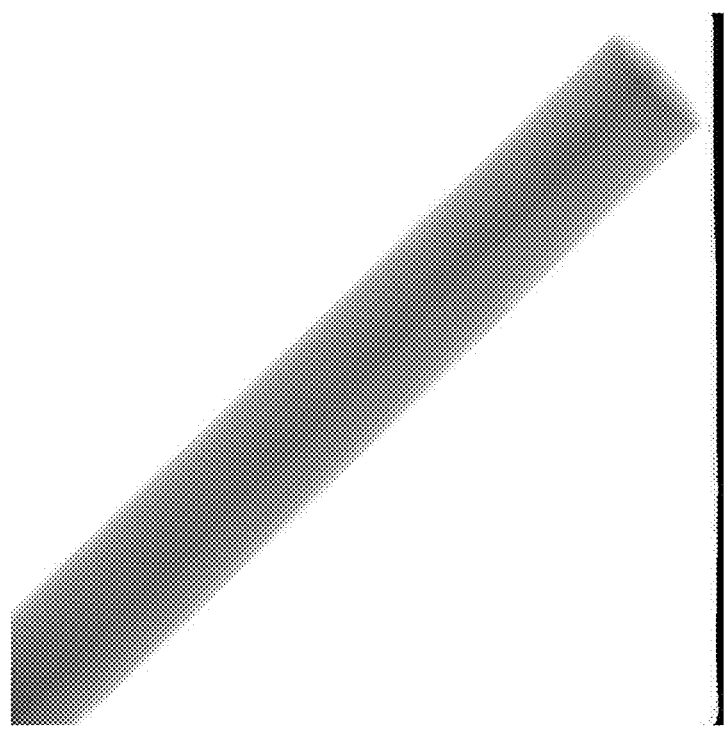
FIG. 7 shows an example of a radiograph of a wood billet.
Figure 8:
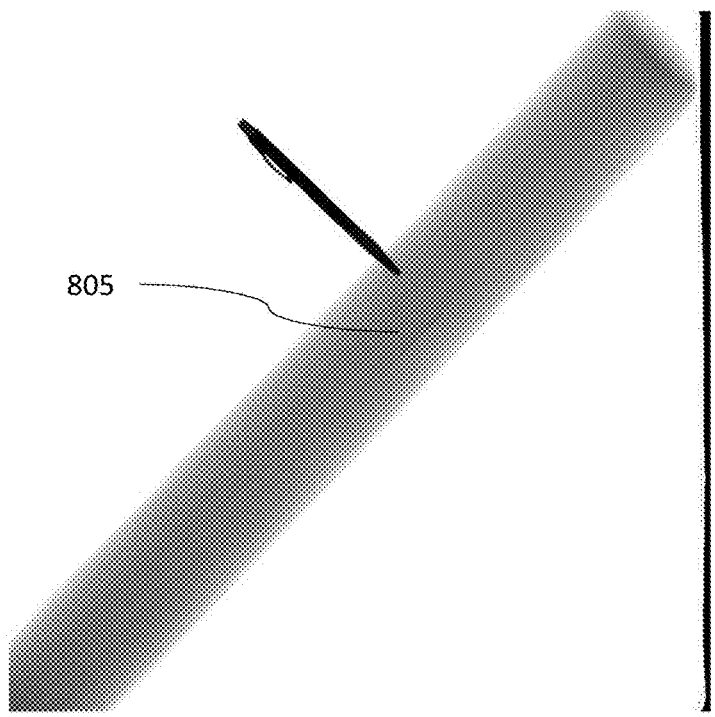
FIG. 8 shows an example of a radiograph of a wood billet with a defect highlighted.

FIG. 7 shows a radiograph of a wood billet. FIG. 8 highlights an anomaly 805 of the material of the billet shown in FIG. 7.

Figure 9:
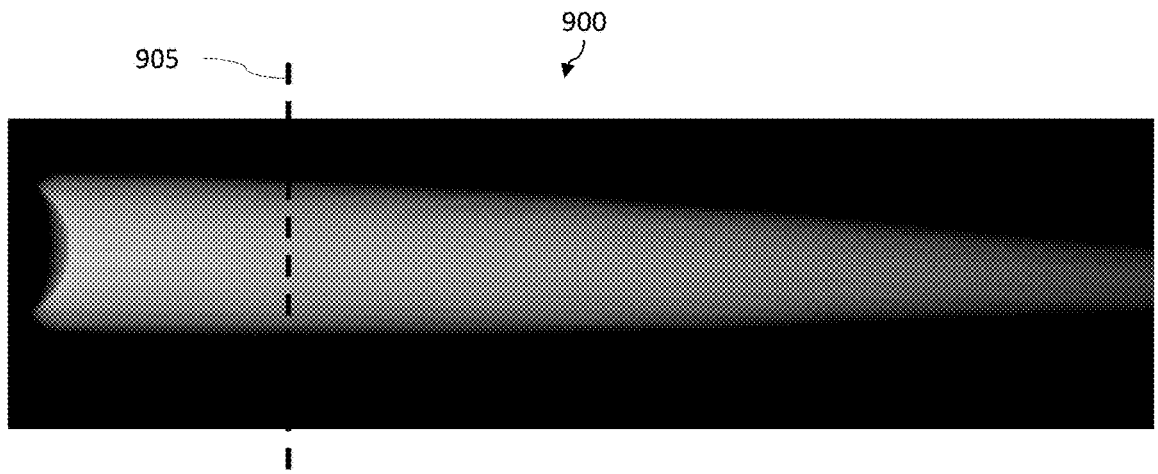
FIG. 9 shows another example of a radiograph of a wood bat.
Figure 10:
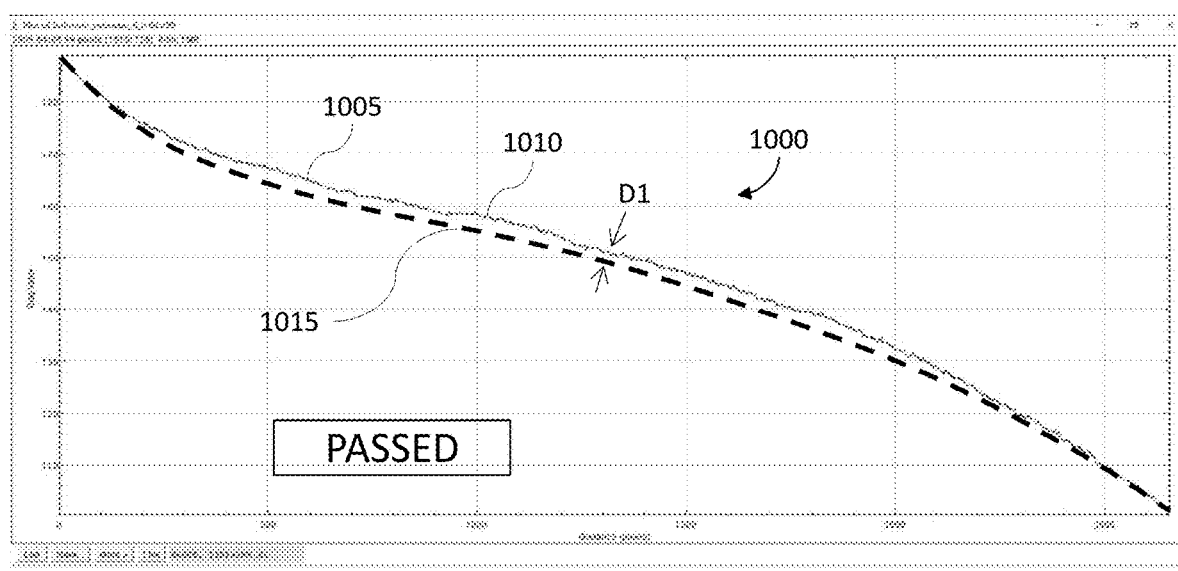
FIG. 10 shows an example of a density plot of a wood bat showing homogeneity.

The radiograph image may be generated by using the controller 430, 530 to read the pixels of the detector 420, 520 and display them with a color or brightness corresponding to an amount of X-ray energy attenuated by the sample 415, 515. FIG. 9 shows an exemplary radiograph 900 of a bat. The density values may be calculated by averaging the Gray value of pixels perpendicular to a length of a scan of the material being analyzed. The calculated values may be plotted along the scanned axis. FIG. 10 shows an exemplary density plot 1000 derived from the radiograph of FIG. 9. The Gray value at point 1005 in FIG. 10 may correspond to an average of the energy of pixels along line 905 in FIG. 9. The radiograph and density plot may then be displayed as shown in FIG. 6, block 645.

Referring to block 650 of FIG. 6, model parameters for the scanned material may be calculated from any of the information about the sample material, X-ray system settings, and settings relevant to the imaging process and procedure entered as shown in block 615, and any of data from the initial scan used to optimize the energy of the X-ray source 410, 510, movement of the X-ray source 410, 510, detector energizing and scanning parameters, movement of the detector 420, 520, and any other suitable parameters of the X-ray system determined as a result of the optimization process of block 625. Exemplary model parameters may be embodied as a series of model density values along a length of a scan of the material determined from one or more of the system settings, characteristics of the material used, and an acceptable longitudinal density variation for a particular application, such as a particular finished piece. The model density values along a length of a scan of the material may have a slope and boundaries determined from the type of material and density characteristics required for a specific application, and may be represented as a model density curve.

For example, a model density curve for a blank may be determined by the system settings, characteristics of the material used, and an acceptable longitudinal density variation for a particular application. Using wood as an exemplary material and a finished baseball bat as the application, characteristics of the material may include the type of wood, rings per inch, and modulus of elasticity, and acceptable longitudinal density variation may be approximately 5%±0.5.

An exemplary model density curve 1015 and measured density parameters shown as a measured density curve 1010 of the material being scanned are shown in FIG. 10. As shown in block 655, the difference between the model parameters and the measured parameters of the material being scanned may be calculated. As shown in block 660, the system may determine whether the material is acceptable for a particular application based on the amount of difference between the measured density parameters and the model density parameters, and whether the longitudinal density variation for the particular application is exceeded.

In one or more embodiments, the system may provide an alert indicating whether the material is acceptable or not, for example, by displaying a message on the display 435, 535, providing an audio or tactile alert through the controller, or any other suitable mechanism for indicating whether the material is acceptable or not.

It should be understood that the system may perform at least some of the operations of the exemplary workflow 600 automatically, which may provide faster and more consistent material qualification, more flexibility for an operator or other user of the system, may generally simplify the qualification procedure. The system advantageously provides the ability to qualify material before or early in the production stage, for example at the blank or billet, before considerable resources are expended to produce the finished piece.

FIG. 9 displays a radiograph of material having acceptable parameters, while FIG. 10 shows a density plot 1000, illustrating measured density measurements 1010 of the material of FIG. 9 and a model density curve 1015, calculated from the information and settings described above. The system has determined that the amount of deviation D1 between the measured parameters of the material 1010 and the parameters of the model density curve 1015 is acceptable for the application, in this example, a baseball bat. In some embodiments an alert may be displayed, in this example, the word "PASSED."

Figure 11:
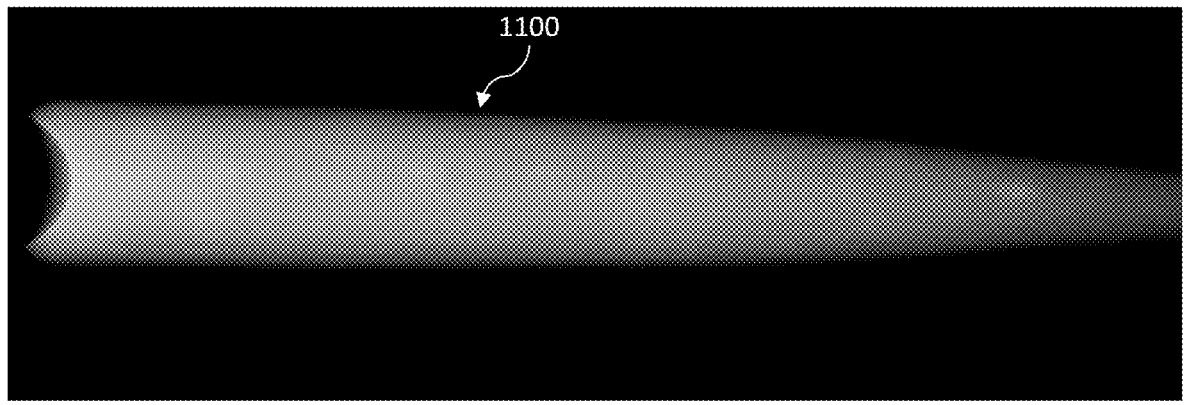
FIG. 11 shows yet another example of a radiograph of a wood bat.
Figure 12:
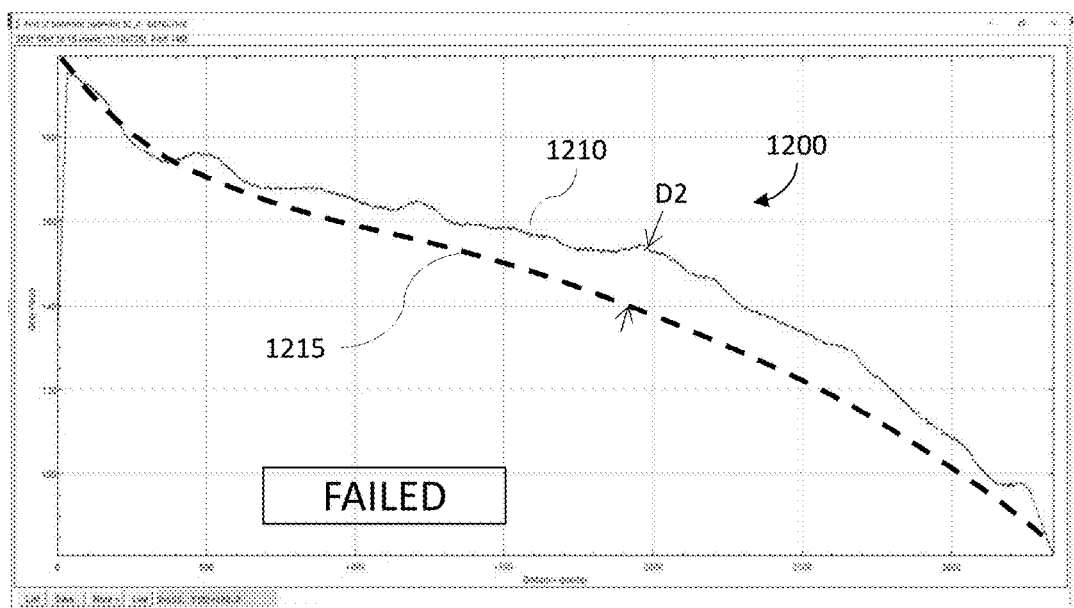
FIG. 12 shows an example of a density plot of a wood bat showing defects.

FIG. 11 displays a radiograph of a defective baseball bat 510. FIG. 12 illustrates a density plot 1200 of the material of FIG. 11 illustrating measured density measurements of the material 1210 and a model density curve 1215, calculated from the information and settings described above. The system has determined that the amount of deviation D2 between the measured parameters of the material 1210 and the parameters of the model density curve 1215 exceeds the allowable deviation for the application, in this example, a baseball bat. In some embodiments an alert may be displayed, in this example, the word "FAILED."

Figure 13A:
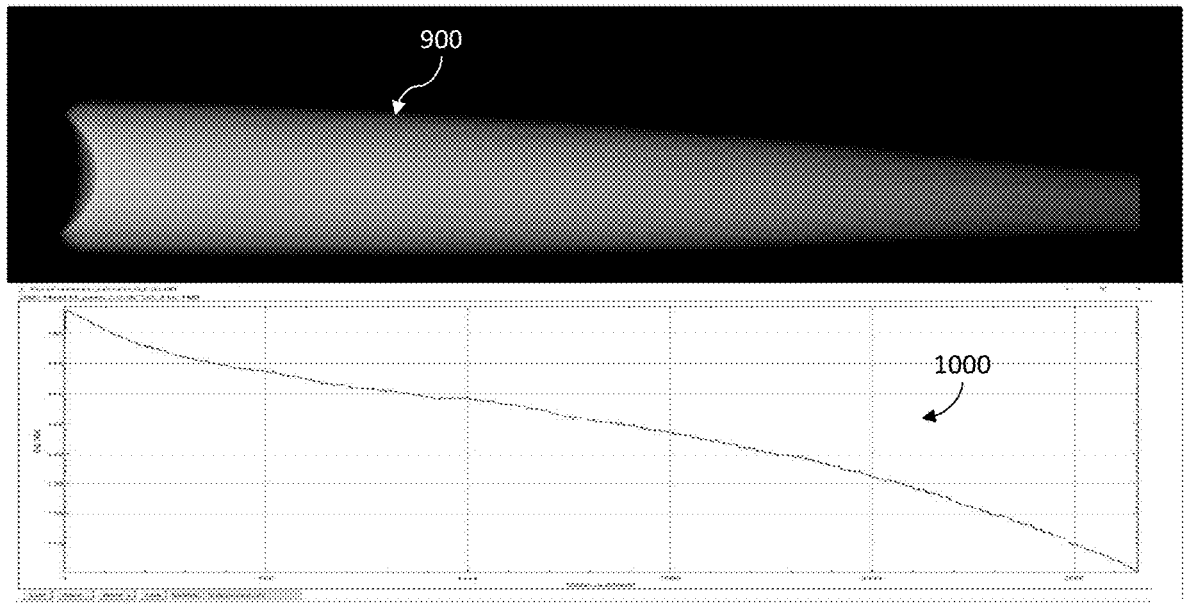
FIG. 13A shows the radiograph of FIG. 9 and the density plot of FIG. 10 displayed adjacent to each other.
Figure 13B:
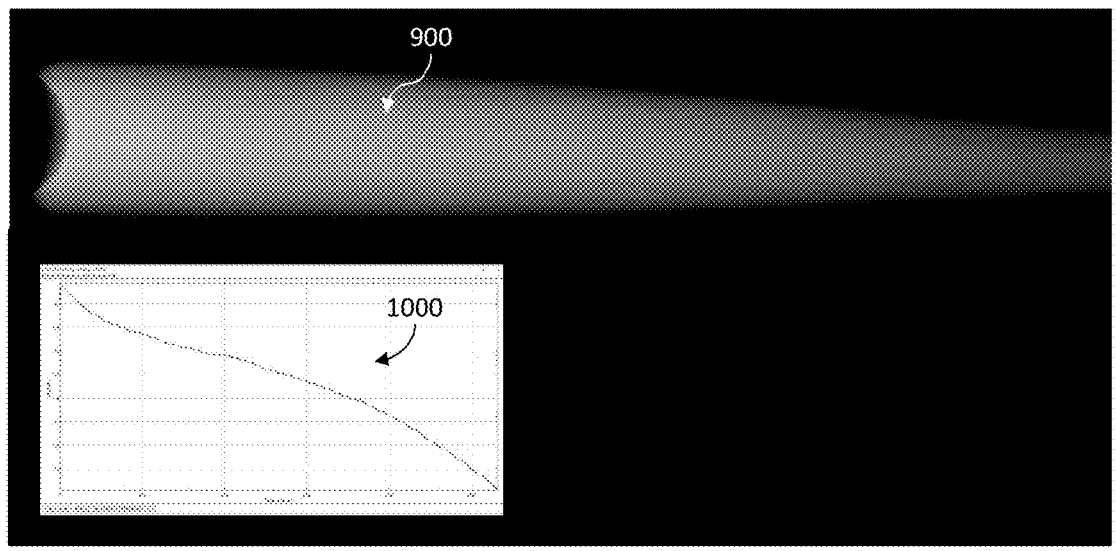
FIG. 13B shows the radiograph of FIG. 9 and the density plot of FIG. 10 displayed in a Picture In Picture (PIP) format.
Figure 13C:
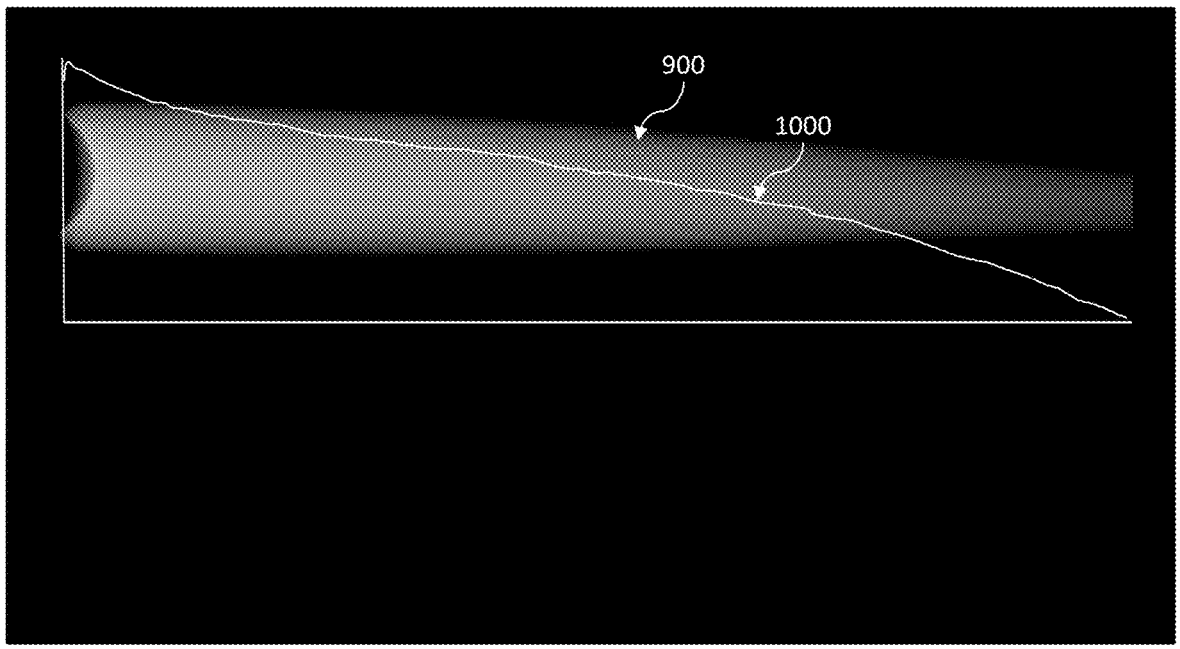
FIG. 13C shows the density plot of FIG. 10 superimposed over the radiograph of FIG. 9.
Figure 14A:
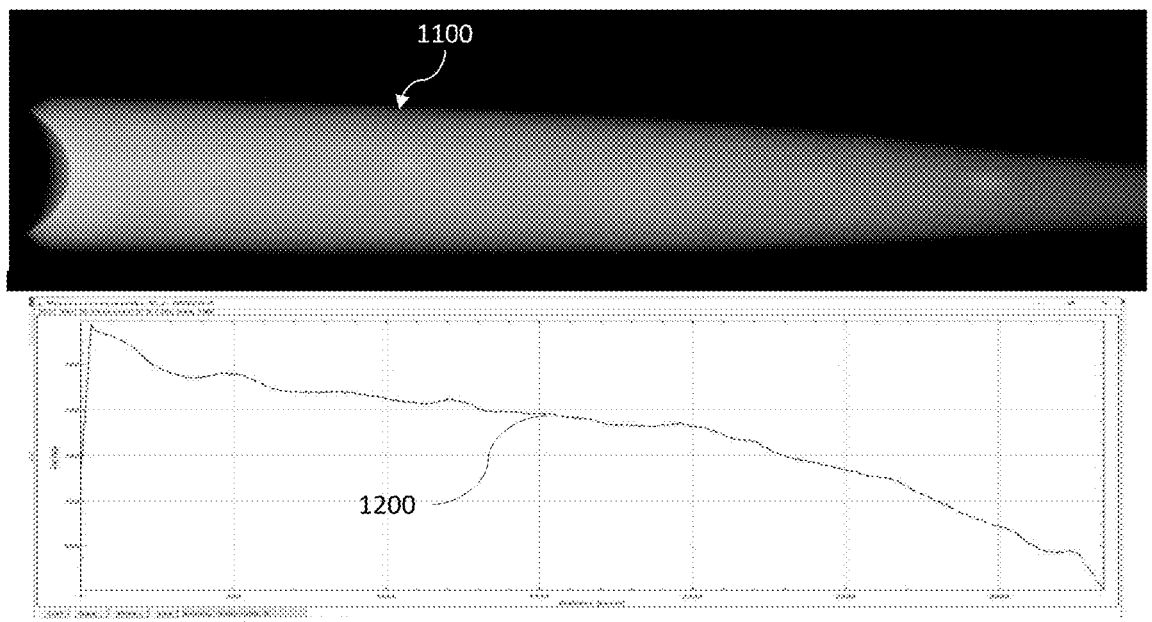
FIG. 14A shows the radiograph of FIG. 11 and the density plot of FIG. 12 displayed adjacent to each other.
Figure 14B:
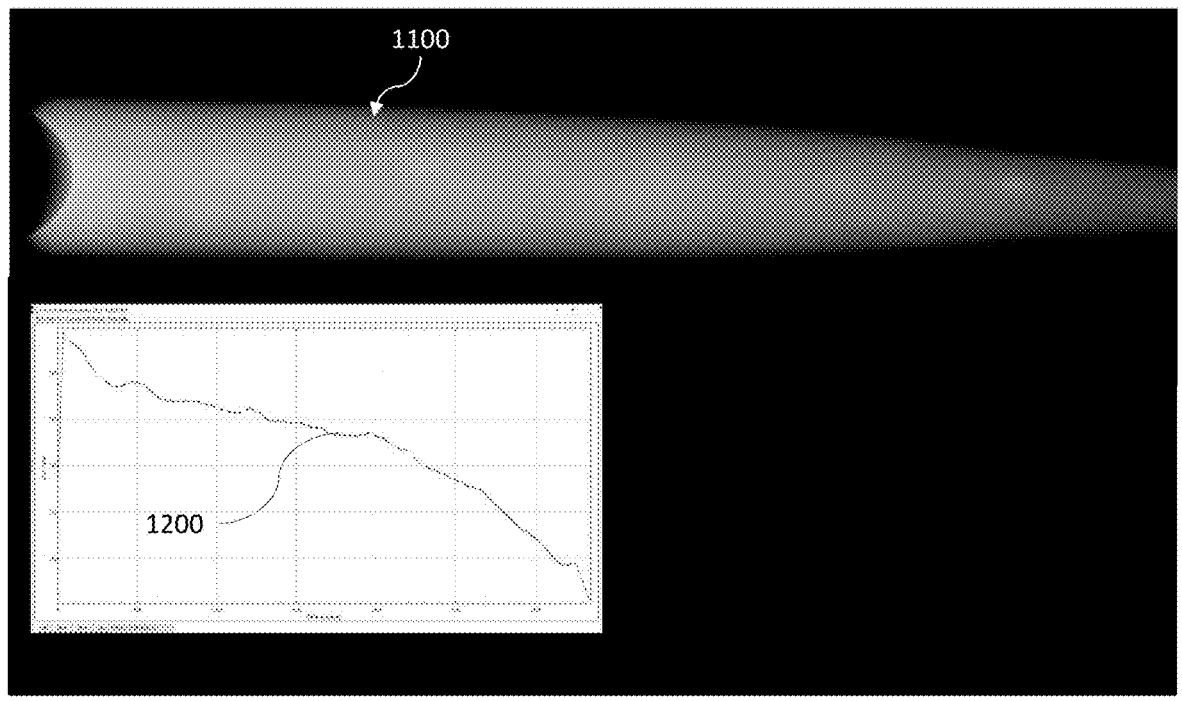
FIG. 14B shows the radiograph of FIG. 11 and the density plot of FIG. 12 displayed in a Picture In Picture (PIP) format.
Figure 14C:
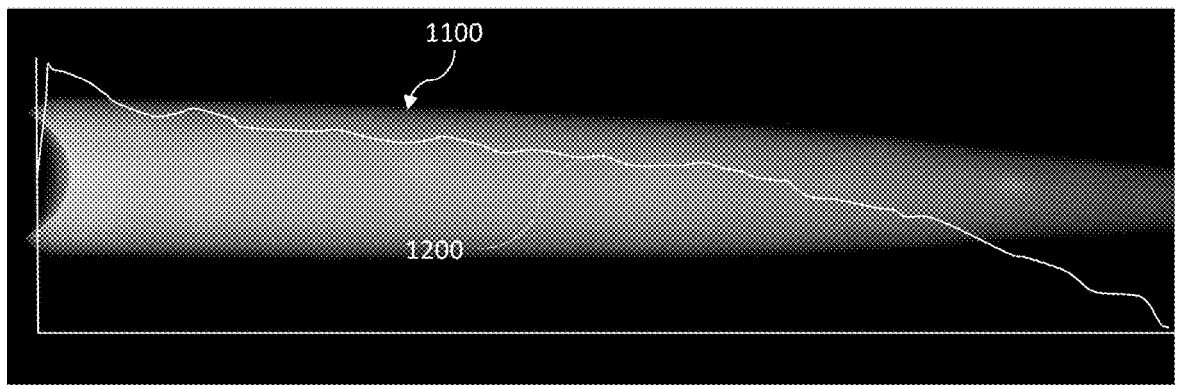
FIG. 14C shows the density plot of FIG. 12 superimposed over the radiograph of FIG. 11.

Returning again to FIG. 6, block 645, the radiograph and density plot may be displayed, for example, on a monitor 435, 535, of controller 430 or 530, respectively. In some embodiments, the radiograph and density plot may be displayed on one or more remote monitors or other display devices which may be remotely connected to the controllers 430, 530. In one or more embodiments, the radiograph and density plot may be generated and displayed concurrently. As shown in FIG. 13A, the radiograph 900 and density plot 1000 may be displayed adjacent to each other on a monitor, while as shown in FIG. 13B, the radiograph 900 and density plot 1000 may be displayed in a Picture In Picture (PIP) format. FIG. 13C illustrates an exemplary display with the density plot 1000 superimposed over the radiograph 900. Similarly, the radiograph 1100 and density plot 1200 may be displayed adjacent to each other on a monitor, as shown in FIG. 14A, while as shown in FIG. 14B, the radiograph 1100 and density plot 1200 may be displayed in a Picture In Picture (PIP) format. FIG. 14C illustrates an exemplary display with the density plot 1200 superimposed over the radiograph 1100. As shown in block 665, the system may optionally display the radiograph, measured density plot, and model density plot, for example, on the monitor 435, 535, of controller 430, 530.

Indeed, it is appreciated that the system and its individual components can include additional features and components, though not disclosed herein, while still preserving the principles of the present invention. Note also that the base controller can be one of any number devices, including a desktop or laptop controller, etc.

The present invention may be embodied in other specific forms without departing from its spirit or essential characteristics. The described embodiments are to be considered in all respects only as illustrative, not restrictive. All changes that come within the meaning and range of equivalency of the claims are to be embraced within their scope.

It is noted that the embodiments described herein can be used individually or in any combination thereof. It should be understood that the foregoing description is only illustrative of the embodiments. Various alternatives and modifications can be devised by those skilled in the art without departing from the embodiments. Accordingly, the present embodiments are intended to embrace all such alternatives, modifications and variances that fall within the scope of the appended claims.

Various modifications and adaptations may become apparent to those skilled in the relevant arts in view of the foregoing description, when read in conjunction with the accompanying drawings. However, all such and similar modifications of the teachings of the disclosed embodiments will still fall within the scope of the disclosed embodiments.

Various features of the different embodiments described herein are interchangeable, one with the other. The various described features, as well as any known equivalents can be mixed and matched to construct additional embodiments and techniques in accordance with the principles of this disclosure.

Furthermore, some of the features of the exemplary embodiments could be used to advantage without the corresponding use of other features. As such, the foregoing description should be considered as merely illustrative of the principles of the disclosed embodiments and not in limitation thereof.

What is claimed is:

1. An X-ray system for analyzing materials comprising:
   an X-ray source;
   an X-ray detector and a sample platform; and
   a controller configured to:
      generate a radiograph of material on the sample platform by selectively energizing the X-ray source to emit X-rays through the material to the X-ray detector along a scanned length of the material;
      calculate a plurality of measured density values along the scanned length of the material;
      calculate a plurality of model density values of the material from one or more of settings of the X-ray system, characteristics of the material along the scanned length of the material, and a longitudinal density variation for a particular application;
      compute a difference between the measured density values and the model density values and determine if the longitudinal density variation has been exceeded; and
      provide an alert as to whether the longitudinal density variation has been exceeded.

2. The X-ray system of claim 1, wherein the X-ray source is a minimum 50 kVp and 1000 μa X-ray source.

3. The X-ray system of claim 1, wherein the X-ray detector comprises a rectangular array of approximately 4318×4320 pixels with a pixel size of 100 micrometers.

4. The X-ray system of claim 1, wherein the controller is configured to calculate the plurality of measured density values by averaging Gray values of detector pixels perpendicular to the scanned length of the material.

5. The X-ray system of claim 1, wherein the material comprises an organic or inorganic material.

6. The X-ray system of claim 1, wherein the material comprises one or more of wood, wood blanks, and wood billets.

7. The X-ray system of claim 1, wherein the material comprises one or more of baseball bats, softball bats, cricket bats, and table tennis bats.

8. The X-ray system of claim 1, wherein the alert comprises a message on a display of the controller.

9. The system of claim 1, wherein the controller is configured to concurrently display the radiograph and the plurality of measured density values.

10. The system of claim 1, wherein the controller is configured to display the plurality of measured density values overlaid on the radiograph.

11. A method of using an X-ray system for analyzing materials, the X-ray system comprising an X-ray source, an X-ray detector and a sample platform, and a controller, the method comprising:
   generating a radiograph of material on the sample platform by selectively energizing the X-ray source to emit X-rays through the material to the X-ray detector along a scanned length of the material;
   calculating a plurality of measured density values along the scanned length of the material;
   calculating a plurality of model density values of the material from one or more of settings of the X-ray system, characteristics of the material along the scanned length of the material, and a longitudinal density variation for a particular application;
   computing a difference between the measured density values and the model density values and determine if the longitudinal density variation has been exceeded; and
   providing an alert as to whether the longitudinal density variation has been exceeded.

12. The method of claim 11, wherein the X-ray source is a minimum 50 kVp and 1000 μa X-ray source.

13. The method of claim 11, wherein the X-ray detector comprises a rectangular array of approximately 4318×4320 pixels with a pixel size of 100 micrometers.

14. The method of claim 11, further comprising calculating the plurality of measured density values by averaging Gray values of detector pixels perpendicular to the scanned length of the material.

15. The method of claim 11, wherein the material comprises an organic or inorganic material.

16. The method of claim 11, wherein the material comprises one or more of wood, wood blanks, and wood billets.

17. The method of claim 11, wherein the material comprises one or more of baseball bats, softball bats, cricket bats, and table tennis bats.

18. The method of claim 11, comprising providing an alert as a message on a display of the controller.

19. The method of claim 11, further comprising concurrently displaying the radiograph and the plurality of measured density values.

20. The method of claim 11, further comprising displaying the plurality of measured density values overlaid on the radiograph.

* * * * *